United States Patent [19]

Karczmer

[11] Patent Number: 4,795,432

[45] Date of Patent: Jan. 3, 1989

[54] SHIELD ASSEMBLY FOR HYPODERMIC INJECTION DEVICES

[76] Inventor: Claude M. Karczmer, 182-25 Tudor Rd., Jamaica Estates, N.Y.

[21] Appl. No.: 16,343

[22] Filed: Feb. 19, 1987

[51] Int. Cl.4 .............................................. A61M 5/32
[52] U.S. Cl. .................................. 604/110; 604/198; 604/263
[58] Field of Search ..................... 604/110, 192–198, 604/263

[56] References Cited

U.S. PATENT DOCUMENTS

| 1,779,451 | 10/1930 | Sponsel | 604/197 |
|---|---|---|---|
| 2,847,995 | 8/1954 | Adams | 604/198 |
| 2,876,770 | 3/1959 | White | 604/198 |
| 2,888,924 | 6/1959 | Dunmire | 604/196 |
| 2,925,083 | 2/1960 | Craig | 604/197 |
| 3,134,380 | 5/1964 | Armao | 604/198 |
| 3,672,368 | 6/1972 | Schwarz | 56/14.4 |
| 3,884,230 | 5/1975 | Wulff | 604/198 |
| 3,890,971 | 6/1975 | Leeson et al. | 604/198 |
| 4,139,009 | 2/1979 | Alvarez | 604/198 |
| 4,233,975 | 11/1980 | Yerman | 604/110 |
| 4,266,543 | 5/1981 | Blum | 604/263 |
| 4,416,663 | 11/1983 | Hall | 604/198 |
| 4,425,120 | 1/1984 | Sampson et al. | 604/198 |
| 4,507,117 | 3/1985 | Vining et al. | 604/197 |
| 4,564,054 | 1/1986 | Gustavsson | 604/198 X |
| 4,573,976 | 3/1986 | Sampson et al. | 604/198 |
| 4,655,751 | 4/1987 | Harbaugh | 604/198 |
| 4,664,259 | 5/1987 | Landis | 604/192 X |
| 4,664,654 | 5/1987 | Strauss | 604/198 |
| 4,695,274 | 9/1987 | Fox | 604/198 |

Primary Examiner—Dalton L. Truluck
Attorney, Agent, or Firm—Bacon & Thomas

[57] ABSTRACT

An automatic shield assembly for preventing reuse of a hypodermic needle injection device, such as a hypodermic syringe or an intravenous needle. A shield member is spring-biased outwardly towards the sharp end of the needle and maintained in this position by a retainer member which is automatically released upon application of the needle to the patient and permits the shield member to enclose and lock the needle against subsequent use upon removal of the needle from the patient.

14 Claims, 5 Drawing Sheets

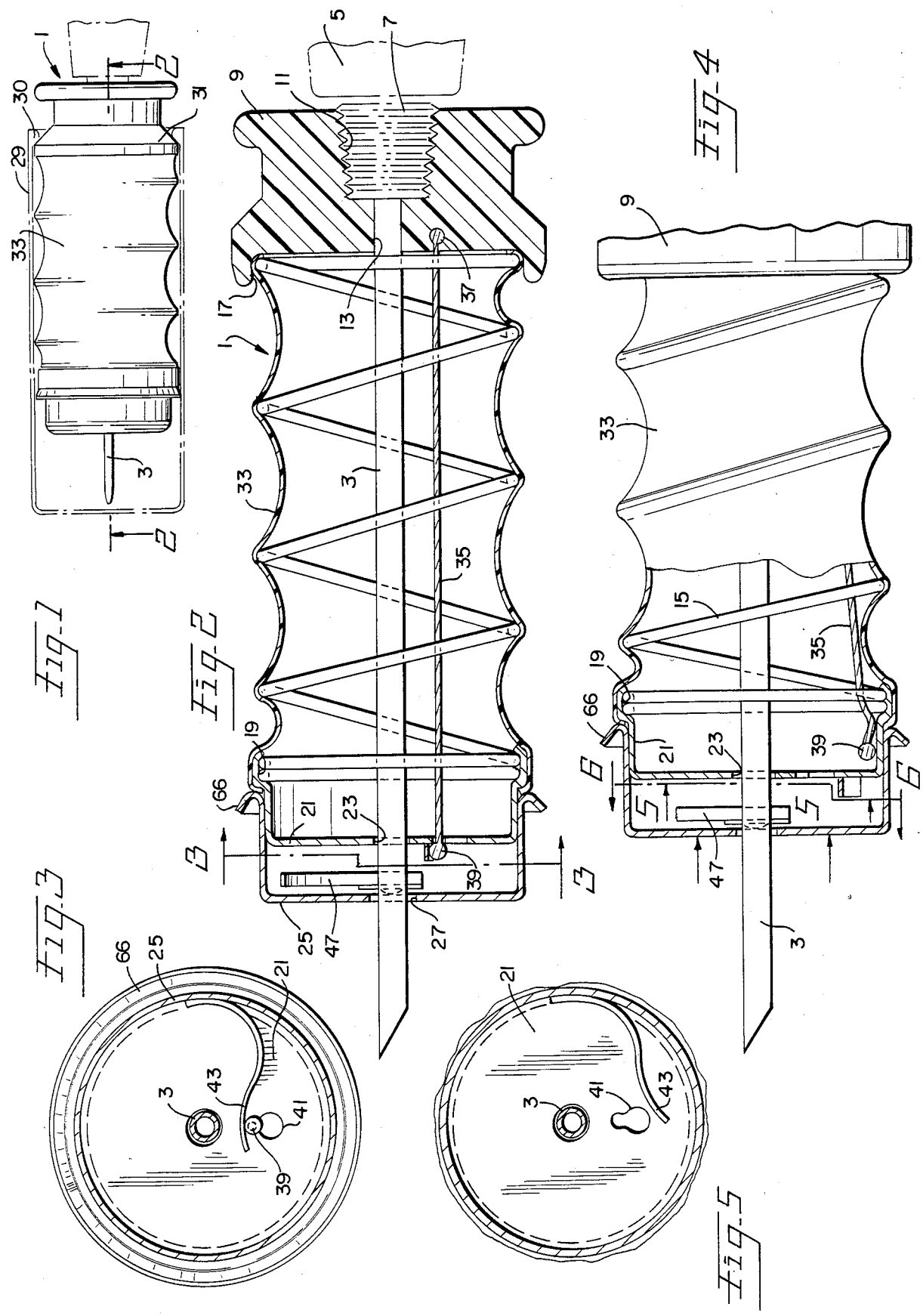

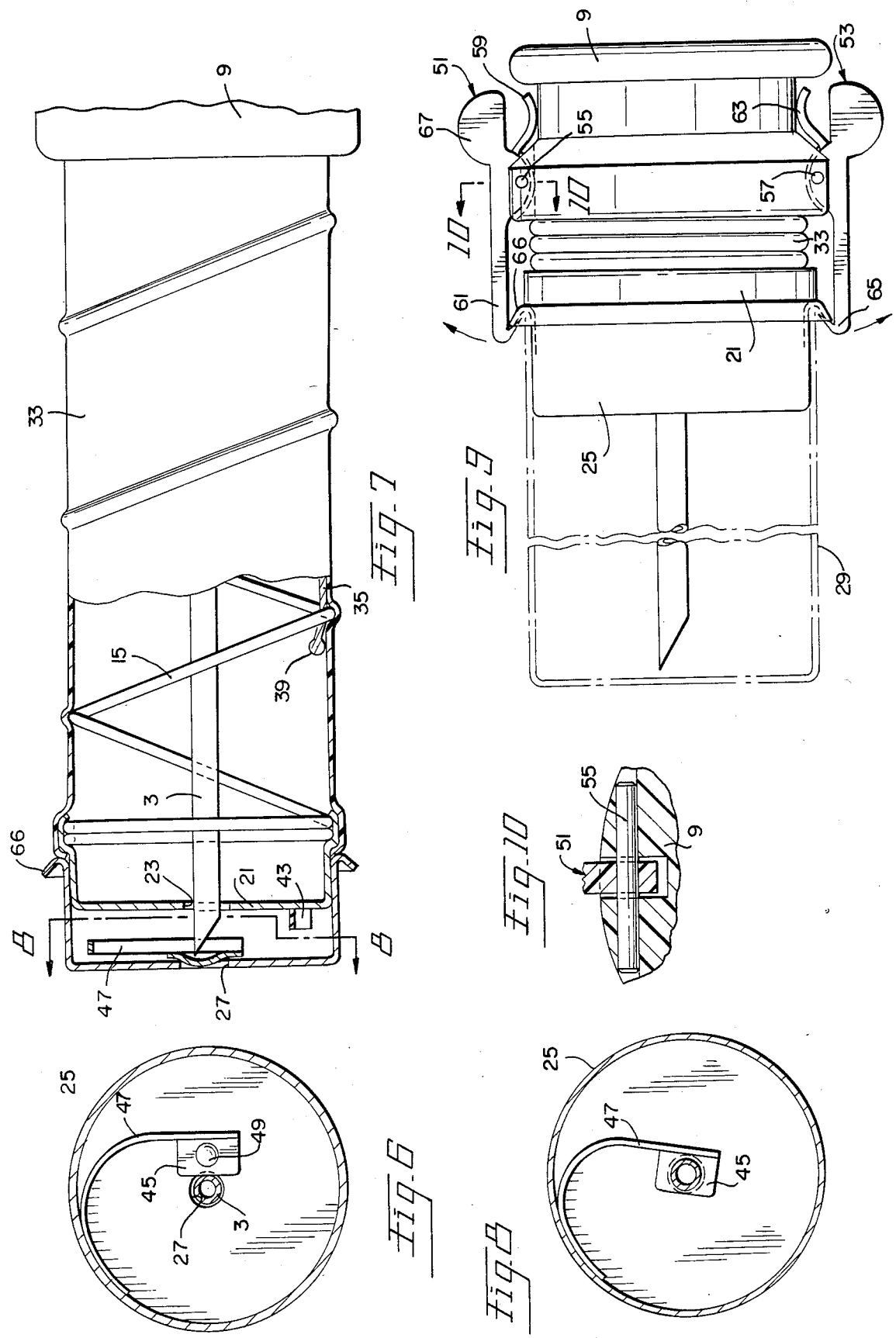

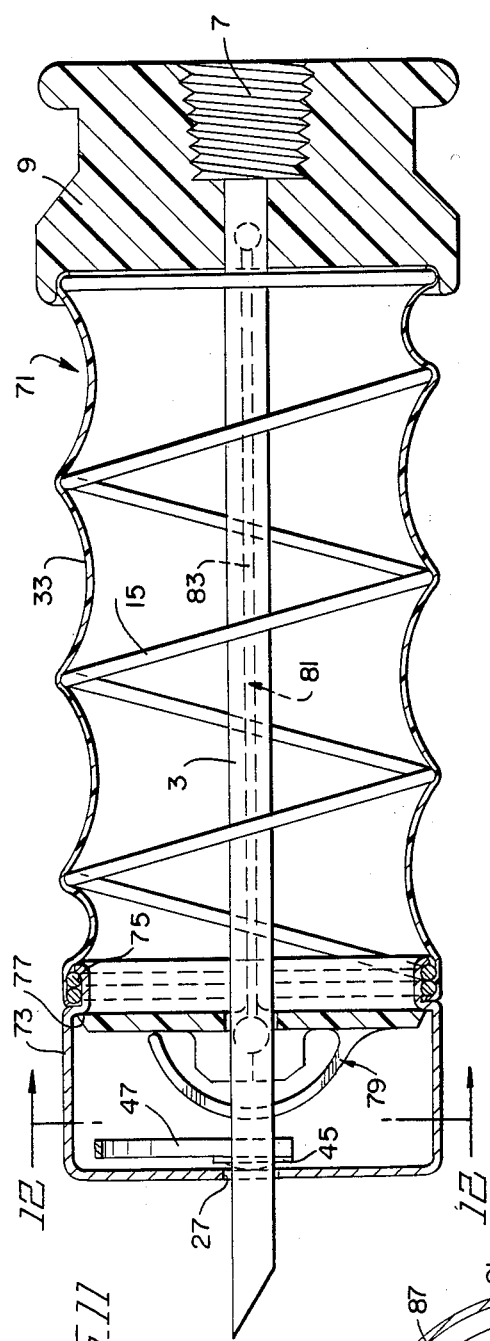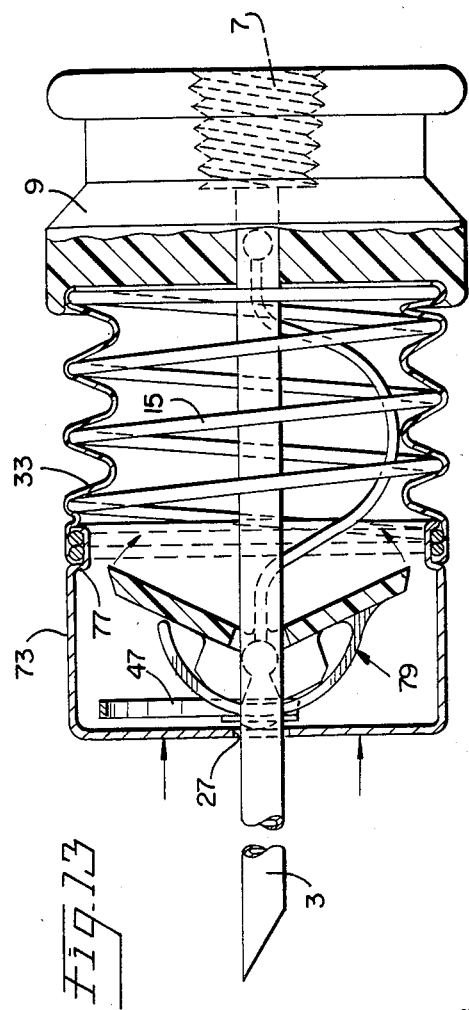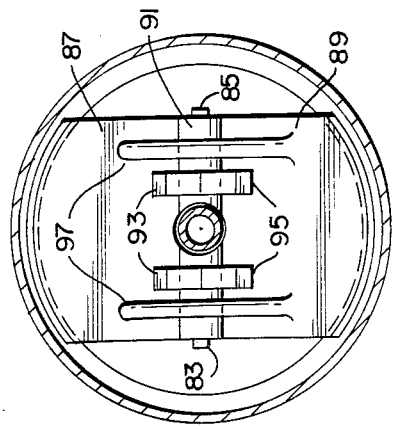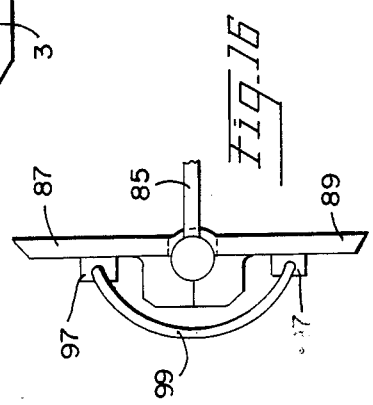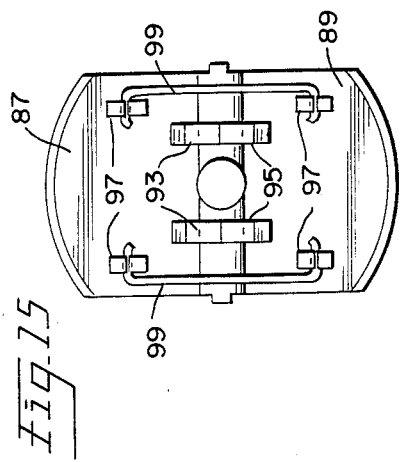

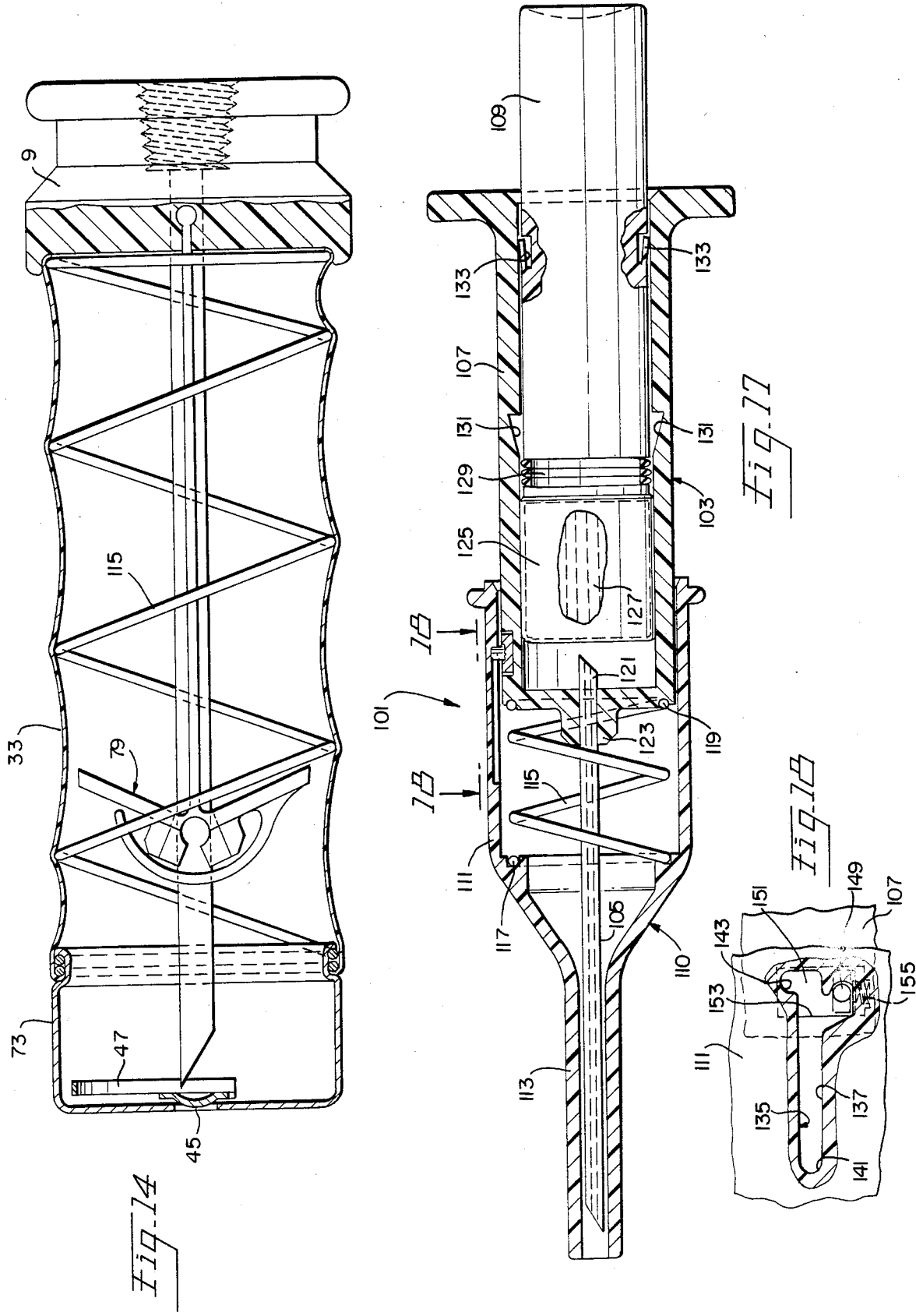

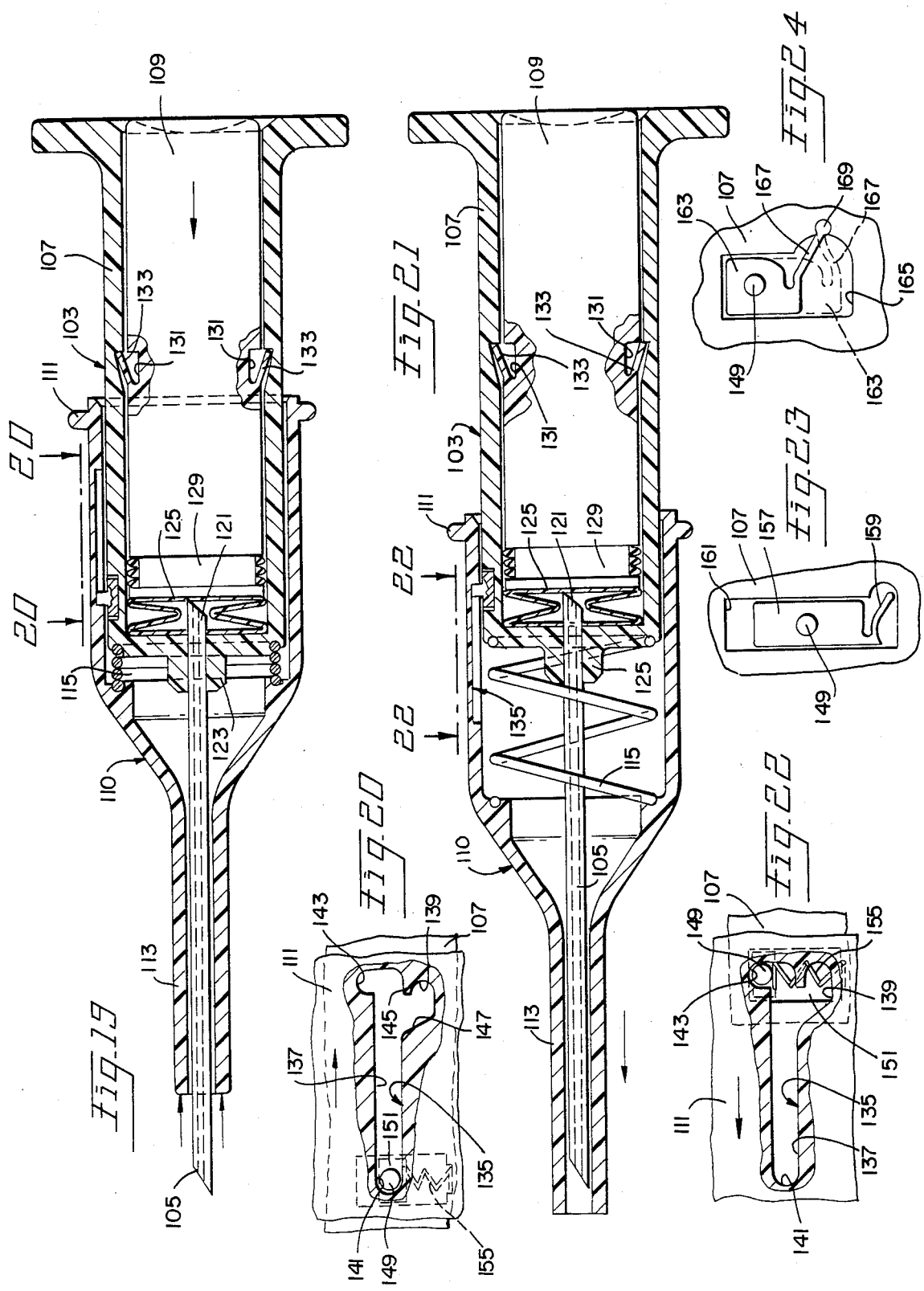

SHIELD ASSEMBLY FOR HYPODERMIC INJECTION DEVICES

BACKGROUND OF THE INVENTION

1. Field of the Invention

The present invention generally involves the field of technology pertaining to devices for the hypodermic injection of medications into a human or animal patient. More particularly, the invention relates to an improved shield assembly for hypodermic injection devices provide with an automatically engageable shield member for preventing reuse of such devices.

2. Description of the Prior Art

Devices for injecting a medication into the body of a human or animal patient are well known. Such devices include hypodermic syringes which receive a quantity of the medication to be injected from an ampoule, and intravenous needles which are inserted into the patient for continuous administration of a treatment substance from a supply container under gravitational flow. Because these devices utilize injection needles, they are generally of a disposable nature and therefore discarded after a single use. It is important that an individual responsible for the safe disposition of the discarded devices be protected from the sharp ends of the needles so that inadvertent injury will not occur. This is particularly critical when the needles have been applied to patients capable of contaminating the needles with blood-transmitted diseases, such as hepatitis or aquired immune deficiency syndrome. It is further important that such hypodermic devices be prevented from being reused by unauthorized individuals.

It is known to provide a hypodermic needle with a cover or shield for preventing inadvertent injury caused by the sharp end of the needle, reuse of the needle or contamination of the needle. These known devices typically require manual removal or replacement and, in some cases, manual adjustment for their disposition either before or after application of the hypodermic needle.

SUMMARY OF THE INVENTION

It is an object of the present invention to provide an improved shield assembly for the needle of a hypodermic injection device whereby the device is automatically prevented from reuse.

It is another object of the invention to provide an improved shield assembly for a hypodermic device which is automatically implemented upon application and removal of the needle with respect to the patient.

It is a further object of the invention to provide an improved shield for the needle of a hypodermic device wherein the shield prevents inadvertent injury and contamination from the sharp end of the needle after a single use of the device.

These and other objects of the invention are realized through an improved shield assembly which is carried by the hypodermic injection device and includes a shield member which surrounds and is axially movable with respect to the needle. The shield member is spring-biased outwardly into a first position and maintained in such a position by a releasable retainer member. During application of the needle to the patient, the shield member is urged inwardly against spring-bias, causing automatic release of the retainer member. When the needle is removed from the patient, the shield member is again urged outwardly under spring-bias to fully enclose the needle. The shield member is automatically locked against subsequent inward movement by a locking member, thereby preventing reuse of the device.

In a first embodiment, the retainer member includes an elongated flexible tether anchored at one end to a base and releasably anchored at the other end within an aperture provided in a retainer housing carried by the shield member. The locking member includes a spring-biased cap which covers an aperture provided in the shield member and through which the needle is disposed. In a second embodiment, the retainer member includes a spring-biased module defined by two hinged flaps which engages an inwardly directed peripheral flange carried by the shield member. In a third embodiment, the shield member includes a track formed in its internal wall for receiving a spring-biased guide pin carried in the external wall of a hypodermic syringe barrel. The track is configured to permit a single retraction of the shield member during application of the needle, after which the guide pin is disposed within a recess of the track to automatically locked the shield member in its final outward position.

Other objects, advantages and features of the invention shall become apparent from the following detailed description of several preferred embodiments thereof, when taken in conjunction with the drawings wherein like reference characters refer to corresponding parts in the several views.

BRIEF DESCRIPTION OF THE DRAWINGS

FIG. 1 is a longitudinal side elevational view of a shield assembly according to a first embodiment of the invention, shown mounted on the needle of a hypodermic syringe and provided with a removable protective cover depicted in phantom lines;

FIG. 2 is an enlarged longitudinal sectional view, partly in elevation, of the shield assembly shown in FIG. 1, with the protective cover removed and retainer member in position prior to application of the needle;

FIG. 3 is a transverse vertical sectional view, taken on the line 3—3 of FIG. 2;

FIG. 4 is a longitudinal sectional view, partly in elevation, showing the shield member being urged inwardly under spring bias, and with the retainer member in its released position;

FIG. 5 is a transverse vertical sectional view, taken on the line 5—5 of FIG. 4;

FIG. 6 is a transverse vertical sectional view, taken on the line 6—6 of FIG. 4, showing the spring-biased locking cap disposed away from the aperture of the shield member by the presence of the needle;

FIG. 7 is a longitudinal sectional view, partly in elevation, showing the shield member in its final position after removal of the needle from the patient, and with the locking cap covering the needle aperture;

FIG. 8 is a transverse vertical sectional view, showing the locking cap in position over the needle aperture and taken on the line 8—8 of FIG. 7;

FIG. 9 is a fragmentary view of the shield assembly of FIG. 1 provided with locking members for securing the shield member in an inwardly compressed position;

FIG. 10 is an enlarged fragmentary vertical sectional view, taken on the line 10—10 of FIG. 9;

FIG. 11 is a longitudinal sectional view of a shield assembly according to a second embodiment of the invention, shown with the retainer member in position;

FIG. 12 is a transverse vertical sectional view, taken on the line 12—12 of FIG. 11;

FIG. 13 is a longitudinal sectional view, partly in elevation, showing the shield assembly of FIG. 11 with the retainer member being released during inward movement of the shield member;

FIG. 14 is a longitudinal sectional view, partly in elevation, showing the shield assembly of FIG. 11 after removal of the needle from the patient and with the shield member in its locked position fully enclosing the sharp end of the needle;

FIG. 15 is a plan view of a modified form of a release module forming a part of the retainer member shown in FIG. 11;

FIG. 16 is a side elevational view of the release module shown in FIG. 15;

FIG. 17 is a longitudinal sectional view, partly in elevation, of a shield assembly according to a third embodiment of the invention, shown with the shield member in an unlocked position prior to application of the needle to the patient;

FIG. 18 is an enlarged fragmentary plan view, with a portion broken away to show the track and spring-biased guide pin in its first position, and taken on the line 18—18 of FIG. 17;

FIG. 19 is a longitudinal sectional view, partly in elevation, showing the shield assembly of FIG. 17 being urged inwardly during application of the needle to the patient;

FIG. 20 is an enlarged fragmentary plan view, with a portion broken away to show the spring-biased guide pin in its second position, as taken on the line 20—20 of FIG. 19;

FIG. 21 is a longitudinal sectional view, partly in elevation, showing the shield member in its locked position upon withdrawal of the needle from the patient;

FIG. 22 is an enlarged fragmentary plan view, with a portion broken away, showing the spring-biased guide pin in its third and locked position, and taken on the line 22—22 of FIG. 21; and FIGS. 23 and 24 are plan views of modified forms of the spring-biased guide pin which may be utilized in the shield assembly of FIG. 17.

DETAILED DESCRIPTION OF THE PREFERRED EMBODIMENTS

A shield assembly 1 according to a first embodiment of the invention shall now be described with initial reference to FIGS. 1-5. As depicted in FIGS. 1 and 2, assembly 1 is shown attached to a needle 3 of a hypodermic syringe, only a barrel 5 of which is partially shown. Needle 3 is provided with a hub 7 of conventional design which permits its detachable connection to barrel 5 by means of a standard coupling, such as a Luer lock coupling or bayonet type coupling. Assembly 1 includes a base 9 provided with a recess 11 for receiving hub 7 and a passageway 13 through which needle 3 is disposed. Base 9 may be detachably secured to hub 7 through a mating threaded connection as shown, or any other known connection means deemed appropriate for the practice of the invention. However, it is preferred that base 9 be permanently attached to hub 7.

A coil spring 15 has one end securely seated within an internal peripheral cavity 17 formed in base 9. Spring 15 surrounds needle 3 which is axially disposed therethrough. The other end of spring 15 is secured within an inwardly directed flanged groove 19 of a retainer housing 21, the latter being also provided with a central aperture 23 through which needle 3 is disposed. Housing 21 is preferably of a substantially cup-shaped configuration. A shield member 25 of substantially the same configuration as housing 21 is coaxially secured to the exterior wall of housing 21, with shield member 25 being also provided with an aperture 27 through which needle 3 is disposed. A removable protective cover 29 is provided for protecting assembly 1 prior to use. Cover 29 may include an inwardly directed rib 30 for snap fitting onto a peripheral ledge 31 of base 9. A cylindrical shroud 33 formed of thin flexible material, such as plastic, surrounds spring 15 and has its respective ends secured within cavity 17 and around the exterior of groove 19. The opposite ends of shroud 33 may be secured in any conventional manner, such as through the use of an appropriate adhesive and a circular band clamp. It is therefore apparent that shroud 33 functions in the manner of a bellows when spring 15 is compressed or expanded during joint movement of both retainer housing 21 and shield member 25 axially of needle 3.

In the position of shield member 25 as shown in FIG. 2, shield member 25 is spring-biased towards the sharp end of needle 3, but is maintained under such bias in its indicated position by means of a retainer member 35, the latter being a tether and preferably formed from a length of flexible material, such as nylon cord or the like. The length of member 35 is such as to permit sufficient exposure of needle 3 for the purpose of withdrawing medication from an ampoule and application of needle 3 to the patient. One end of member 35 is provided with an enlarged knob 37 which is preferably anchored to base 9 through any conventional molding technique. The other end of member 35 is also provided with an enlarged knob 39 which is releasably secured against the edges of the smaller portion of a substantially figure eight-shaped aperture 41 having different sized portions and provided in retainer housing 21. This is more clearly shown in FIGS. 3 and 5 wherein, as particulary seen in FIG. 3, knob 39 is retained against housing 31 by being disposed against the smaller portion of the aperture 43 under the bias of spring 15. A release spring 43, in the form of a leaf spring, is carried by shield member 25 for the purpose of engaging knob 39 and biasing same towards the large portion of aperture 42. The bias force of spring 43 is not sufficient to move knob 39 from its position shown in FIG. 3 because of the greater bias force imposed by spring 15. However, as shown in FIG. 4, when shield member 25 is caused to be urged inwardly against the bias of spring 15 during application of needle 3 to a patient, the tension in retainer member 35 is immediately removed, thereby permitting release spring 43 to automatically push knob 39 towards the larger portion of aperture 41 and causing its release therethrough, as seen in FIG. 5. Since retainer member 35 now remains completely unattached within shroud 33, it is therefore clear that removal of needle 3 from the patient shall immediately cause shield member 25 to move outwardly towards the end of needle 3 due to the bias provided by spring 15. Because retainer member 35 is no longer present to limit the outward movement of shield member 25, the latter is therefore permitted to extend completely beyond the sharp end of needle 3 and enclose same, as shown in FIG. 7.

In order to fully protect and enclose the end of needle 7 against contamination and reuse, a cap 45 is carried at one end of a leaf spring 47. The other end of spring 47 is attached to shield member 25. Cap 45 is preferably provided with a hollow dimple 49 sized to interlock within aperture 27 of member 25, as seen in FIG. 7. As evident in FIG. 6, when needle 3 extends through aperture 27, cap 45 is caused to engage the side of needle 3 under the bias of spring 47. When needle 3 is withdrawn from aperture 27, cap 45 is thereby automatically snapped into position, thereby closing aperture 27 and preventing subsequent access to the sharp end of needle 3. Shield assembly 1 and needle 3, as shown in FIG. 7, may thereafter be safely handled and discarded without the danger of inadvertent injury or contamination to persons handling same. This is because the shield member 25 and cap 45 securely lock the sharp end of needle 3 within shield member 25 and, along with shroud 33, serve to fully enclose needle 3 and retain excess liquids therein.

A slightly modified form of shield assembly 1 is shown in FIGS. 9 and 10. In this case, base 9 is provided with a pair of locking levers 51 and 53 that are pivotally attached to base 9 by a pair of corresponding pins 55 and 57. Lever 51 includes a leaf spring 59 for biasing a hook 61 inwardly towards needle 3. Similarly, lever 53 is also provided with a leaf spring 63 for biasing a hook 65 inwardly towards needle 3. In this way, shield member 25 may be fully retracted inwardly to compress shroud 33 and spring 15 and maintained in this position by securing hooks 61 and 65 onto a peripheral flange 66. Release of shield member 25 is accomplised by manually compressing a pair of tabs 67 and 69 carried by levers 51 and 53, respectively, against the bias imposed by corresponding springs 59 and 63. This modification permits shroud 33 to be locked in a compressed condition prior to application of needle 3 in order to afford better access to needle 3 for certain procedures. After withdrawal of needle 3 from the patient, levers 51 and 53 may be actuated to release shield member 25 for its full outward extension to the position shown in FIG. 7.

A shield assembly according to a second embodiment of the invention shall now be described with initial reference to FIGS. 11-14. As particularly noted in FIGS. 11 and 12, assembly 71 is substantially the same as assembly 1 of the first embodiment except for two basic differences. In this case, a shield member 73 is provided with an outwardly directed flanged groove 75 within which corresponding ends of spring 15 and shroud 33 are securely attached. Groove 75 is also partially defined by an inwardly directed peripheral ledge 77 against which a release module 79, forming a part of a retainer member 81, may be releasably secured. Member 81 includes an opposed pair of flexible tethers 83 and 85 which have one pair of corresponding ends connected to module 79 and the other pair of corresponding ends secured in base 9 in the same manner previously described for assembly 1. Module 79 includes a pair of flaps 87 and 89 joined at a hinge line 91. It is preferred that flaps 87 and 89 be integrally molded from appropriate plastic material whereby hinge line 91 may be defined by a thin integral portion of such material. Flap 87 is provided with a pair of stops 93 which are engageable against a corresponding pair of opposed stops 95 carried by flap 89 for the purpose of limiting the outward pivotal movement of flaps 87 and 89 about hinge line 91 to the coplanar relationship shown in FIG. 1. Flaps 87 and 89 are also provided with a pair of springs 97 which serve to bias flaps 87 and 89 towards a closed position. It is further preferred that stops 93 and 95, and springs 97 be integrally molded with flaps 87 and 89.

The position of shield assembly 71 shown in FIG. 11 is that prior to application of needle 3 to the patient. As indicated, the sharp end of needle 3 extends for a sufficient distance from aperture 27 of shield member 73 in order to permit the withdrawal of the substance to be injected from an ampoule or similar source. In this position, flaps 87 and 89 are disposed in their unfolded and coplanar relationship against the bias of springs 97 and engaged upon peripheral ledge 77 under the bias of coil spring 15. Upon application of needle 3 to the patient, shield member 73 is retracted inwardly as shown in FIG. 13. This causes the immediate slackening of tethers 83 and 85, and the folding of flaps 87 and 89 inwardly under the bias of springs 97. Accordingly, flaps 87 and 89 are therefore released from peripheral ledge 77, thereby causing module 79 to fall freely within shroud 33. This latter position is indicated in FIG. 14 wherein needle 3 has been removed from the patient and shield member 73 is caused to extend outwardly under the bias of spring 15 to a position wherein it fully encloses the sharp end of needle 3, with aperture 27 being closed and locked by cap 45 in the same manner as previously described.

A modified form of module 79 is shown in FIGS. 15 and 16. In this case, flaps 87 and 89 are each provided with a pair of slotted tabs 97 which secure the opposite inturned ends of a pair of curved springs 99 made of wire or other suitable material. Tabs 97 are preferably integally molded with flaps 87 and 89.

A shield assembly 101 according to a third embodiment of the invention shall now be described with reference to FIGS. 17-22. In this embodiment, shield assembly 101 is structurally integrated with a hypodermic syringe 103 defined by a needle 105, a barrel 107 and a plunger 109. Shield assembly 101 includes a shield member 110 defined by a cylindrical casing portion 111 which tapers into an elongate nose portion 113 sized for freely receiving needle 105 therethrough. The sharp end of needle 105 may be concealed within the terminal end of nose portion 113. Assembly 101 is also provided with a coil spring 115, one end of which is secured within a peripheral groove 117 formed in the internal wall of casing 111. The other end of spring 115 is secured within a peripheral groove 119 formed within the terminal end of barrel 107, the latter being preferably molded from plastic material. An internal end 121 is secured through a nipple 123 carried at the end of barrel 107. End 121 is provided with a sharp point for penetrating a flexible container 125 and receiving a quantity of injection substance 127 contained therein upon compression of plunger 109 towards needle 105. A gasket assembly 129 of appropriate design is disposed between container 125 and plunger 109. As also seen in FIG. 17, the internal wall of barrel 107 is provided with a pair of opposed recesses 131 for engagement by a pair of outwardly biased tabs 133 carried by plunger 109.

An important aspect of shield assembly 101 resides in the manner in which assembly 101 is locked after withdrawal of needle 105 from the patient in order to prevent its reuse and guard against inadvertent injury from the sharp end of needle 105. This is realized by molding a track 135 of a particular configuration within the internal wall of casing 111. As shown in FIGS. 18, 20 and 22, track 135 includes a longitudinal portion 137, a first recess 139, a second recess 141 defining a terminal end of longitudinal portion 137, and a third recess 143 disposed substantially opposite first recess 139. As more clearly shown in FIG. 20, recess 139 is of semicircular configuration and includes both a gate portion 145 and a ramp portion 147. Second recess 141 is also of semicircular configuration. Third recess 143 is of semicircular configuration and faces in a direction transverse to the longitudinal axis of portion 137. A cylindrical guide pin 149 is carried by a slide 151 which is in turn movably supported within a recess 153 formed in the external wall of barrel 107. Guide pin 149 is disposed within track 135 for travel along longitudinal portion 137 and sequentially engageable within receses 139, 141 and 143. The configuration and size of recess 153 is such that slide 151 is constrained to a limited reciprocal movement in a direction transverse to the longitudinal axis of portion 137 and of sufficient distance to permit pin 149 to engage within opposed recesses 139 and 143. As seen in FIG. 18, slide 151 is maintained under the bias of a spring means 155, such as a coil spring or the like, so that pin 149 is continuously urged towards recess 143, a terminal position of pin 149 as shown in FIG. 22.

In the position of shield member 110 and syringe 103 as shown in FIG. 17, guide pin 149 is disposed within recess 139 and in engagement against gate portion 145 due to the bias imposed by spring 155 against slide 151. When needle 105 of syringe 103 is applied to the patient, shield member 110 is caused to be urged inwardly against the bias of spring 115 as shown in FIG. 19. When plunger 109 is activated to compress container 125 end 121 of needle 105 is caused to puncture container 127. Continued movement of plunger 109 causes substance 127 to be injected through needle 105 and into the patient. When this occurs, guide pin 149 is caused to move forwardly and up ramp portion 147 for disposition into longitudinal portion 137 of track 135 and engagement within recess 141. At this point, tabs 133 on plunger 109 are snapped into recesses 131 of barrel 107, thereby locking plunger 109 within barrel 107 and preventing reuse of syringe 103. When needle 105 is removed from the patient as shown in FIG. 21, shield member 110 is extended outwardly under the bias of spring 115 so that nose portion 113 completely encloses the sharp end of needle 105. During this occurrence, guide pin 149 is caused to move backwardly along longitudinal portion 137 of track 135. Because of the position of gate portion 135 and the bias imposed by spring 155 against slide 151, guide pin 149 is caused to snap into recess 143 wherein it is locked against subsequent removal. In this way, both shield member 110 and plunger 109 are securely locked to prevent reuse of syringe 103 and injury from the sharp end of needle 105.

FIGS. 23 and 24 depict modified forms of slides which may be utilized with shield assembly 101. As seen in FIG. 23, guide pin 149 may be supported for movement on a slide 157 provided with an integral resilient biasing member 159. Slide 157 is supported for movement within a recess 161 that is sized to accommodate the shifting of guide pin 149 within track 135 as previously described herein. It is preferred that guide pin 149 be also integrally molded with slide 157 from an appropriate plastic material. As seen in FIG. 24, a slide 163 supporting guide pin 149 is disposed for sliding movement within a corresponding recess 165. In this case, an integral resilient biasing member 167 has a terminal end 169 secured to the body portion of barrel 107.

It is to be understood that the embodiments of the invention herein shown and described are to be taken as preferred examples of the same, and that various changes in shape, size and arrangement of parts may be resorted to without departing from the spirit of the invention or scope of the subjoined claims.

I claim:

1. A shield assembly for preventing reuse of a hypodermic needle and injury or contamination from contact by the sharp end of the needle, which assembly comprises:
    (a) a shield member for surrounding the needle and enclosing the sharp end thereof, the shield member including an aperture through which the needle is disposed;
    (b) means for biasing the shield member outwardly toward the sharp end of the needle;
    (c) retainer means for retaining the shield member at a fixed position relative to the needle against the bias imparted by the biasing means;
    (d) the retainer means being releasable upon application of the needle to a patient during which the shield member is urged inwardly away from the sharp end of the needle against the bias imparted by the biasing means;
    (e) the shield member being biased outwardly by the biasing means for enclosing the sharp end of the needle during removal of the neelde from the patient; and
    (f) locking means carried by the shield member, which locking means is automatically engaged upon enclosing of the sharp point of the needle by the shield member for preventing access to the sharp point of the needle after the shield member has enclosed same.

2. The shield assembly of claim 1 wherein the biasing means includes a coil spring for surrounding the needle.

3. The shield assembly of claim 2 further including a base for connection to the needle, a retainer housing carried by the shield member, one end of the coil spring being secured to the base and the other end of the coil spring being secured to the retainer housing, and a flexible shroud enclosing the coil spring.

4. The shield assembly of claim 2 further including a base for detachable connection to the needle, one end of the coil spring being secured to the base and the other end of the coil spring being secured to the shield member, and a flexible shroud enclosing the coil spring.

5. The shield assembly of claim 2 further including a syringe barrel and a plunger slidably receivable through one end of the barrel, the needle being carried by the other end of the barrel with an end of the needle extending therethrough, the shield member including a casing portion slidably receivable on the other end of the barrel and enclosing the coil spring therein, and a nose portion carried by the casing portion for enclosing the sharp end of the needle.

6. The syringe assembly of claim 5 further including at least one recess formed in the interior wall of the syringe barrel and at least one outwardly biased tab carried by the plunger for engaging the recess to lock the plunger in a fixed position with respect to the barrel.

7. The syringe assembly of claim 5 wherein the syringe barrel further includes a chamber for receiving a container filled with substance to be injected, and a gasket disposed between the container and plunger.

8. A shield assembly for preventing reuse of a hypodermic needle and injury or contamination from contact by the sharp end of the needle, which assembly comprises:

(a) a shield member for surrounding the needle and enclosing the sharp end thereof, the shield member including an aperture through which the needle is disposed;

(b) means for biasing the shield member outwardly toward the sharp end of the needle;

(c) retainer means for retaining the shield member at a fixed position relative to the needle against the bias imparted by the biasing means;

(d) the retainer means being releasable upon application of the needle to a patient during which the shield member is urged inwardly away from the sharp end of the needle against the bias imparted by the biasing means;

(e) the shield member being biased outwardly by the biasing means for enclosing the sharp end of the needle during removal of the needle from the patient; and (f) a spring-biased cap carried by the shield member for closing off the aperture when the needle is removed therefrom to prevent access to the sharp end of the needle after the shield member has enclosed same.

9. A shield member for preventing reuse of a hypodermic needle and injury or contamination from contact by the sharp end of the needle, which assembly comprises:

(a) a shield member for surrounding the needle and enclosing the sharp end thereof;

(b) a coil spring surrounding the needle for biasing the shield member outwardly toward the sharp end of the needle;

(c) retainer means for retaining the shield member at a fixed position relative to the needle against the bias imparted by the coil spring;

(d) a base for connection to the needle and a retainer housing carried by the shield member;

(e) one end of the coil spring being secured to the base and the other end of the coil spring being secured to the retainer housing;

(f) a flexible shroud enclosing the coil spring;

(g) the retainer means including a flexible elongate tether having one end anchored to the base and the other end being detachably secureable to the retainer housing, with the tether being releaseable upon application of the needle to a patient during which the shield member is urged inwardly away from the sharp end of the needle against the bias imparted by the coil spring;

(h) the shield member being biased outwardly by the coil spring for enclosing the sharp end of the needle during removal of the needle from the patient; and (i) locking means carried by the shield member for preventing access to the sharp end of the needle after the shield member has enclosed same.

10. The shield assembly of claim 9 wherein the retainer housing includes an aperture of a substantially figure eight-shaped configuration having different sized portions, the other end of the tether includes an enlarged knob detachably secureable against the edge of the smaller sized portion of the aperture, and a release spring biasing the enlarged knob toward the larger sized portion of the aperture.

11. A shield assembly for preventing reuse of a hypodermic needle and injury to contamination from contact by the sharp end of the needle, which assembly comprises:

(a) a base for detachable connection to the needle;

(b) a shield member for surrounding the needle and enclosing the sharp end thereof;

(c) a coil spring surrounding the needle for biasing the shield member outwardly toward the sharp end of the needle, one end of the coil spring being secured to the base and the other end of the coil spring being secured to the shield member;

(d) a flexible shroud enclosing the coil spring;

(e) retainer means for retaining the shield member at a flexible position relative to the needle against the bias imparted by the coil spring, the retainer means including an inwardly directed peripheral ledge carried by the shield member, a pair of flexible elongate tethers having one pair of corresponding ends anchored to the base, and a pair of foldable hinged flaps carried by the other corresponding ends of the tethers for detachable engagement against the peripheral ledge when the flaps are disposed in an unfolded coplanar relationship;

(f) the retainer means being releasable upon application of the needle to a patient during which the shield member is urged inwardly away from the sharp end of the needle against the bias imparted by the coil spring;

(g) the shield member being biased outwardly by the coil spring for enclosing the sharp end of the needle during removal of the needle from the patient; and (h) locking means carried by the shield member for preventing access to the sharp end of the needle after the shield member has enclosed same.

12. The shield assembly of claim 11 further including resilient means carried by the flaps for biasing the flaps toward a closed position.

13. A shield assembly of claim 12 further including a pair of stops carried by each flap, wherein the stops of each flap are engageable against the stops of the other flap for maintaining the flaps in the unfolded coplanar relationship.

14. A shield assembly for preventing reuse of a hypodermic needle and injury or contamination from contact by the sharp end of the needle, which assembly comprises:

(a) a syringe barrel and a plunger slidably receivable through one end of the barrel, the needle being carried by the other end of the barrel with an end of the needle extending therethrough;

(b) a shield member for surrounding the needle and enclosing the sharp end thereof;

(c) a soil spring surrounding the needle for biasing the shield member outwardly toward the sharp end of the needle;

(d) the shield member including a casing portion slidably receivable on the other end of the barrel and enclosing the coil spring therein, and a nose portion carried by the casing portion for enclosing the sharp end of the needle;

(e) retainer means for retaining the shield member at a fixed position relative to the needle against the bias imparted by the coil spring;

(f) locking means carried by the shield member for preventing access to the sharp point of the needle after the shield member has enclosed same;

(g) a track formed in the interior wall of the casing portion wherein the track is configured to define first, second and third recesses, a guide pin mounted on a spring-biased slide carried by the syringe barrel, the guide pin being disposable in the first recess for maintaining the shield member in a fixed position relative to the needle for defining the retainer means, and disposable in the third recess for securing the shield member relative to the syringe barrel for defining the locking means;

(h) the retainer means being releasable upon application of the needle to a patient during which the shield member is urged inwardly away from the sharp end of the needle against the bias imparted by the coil spring; and (i) the shield member being biased outwardly by the coil spring for enclosing the sharp point of the needle during removal of the needle from the patient.

* * * * *